(12) United States Patent
Kawabata et al.

(10) Patent No.: US 7,722,605 B2
(45) Date of Patent: May 25, 2010

(54) ABLATION CATHETER

(75) Inventors: Takashi Kawabata, Hasuda (JP);
Tadatsugu Onuma, Kawaguchi (JP);
Yasuo Sakano, Tokorozawa (JP)

(73) Assignee: Japan Lifeline Co., Ltd., Tokyo (JP)

( * ) Notice: Subject to any disclaimer, the term of this patent is extended or adjusted under 35 U.S.C. 154(b) by 291 days.

(21) Appl. No.: 10/587,310

(22) PCT Filed: Jan. 26, 2005

(86) PCT No.: PCT/JP2005/001446

§ 371 (c)(1),
(2), (4) Date: Jul. 26, 2006

(87) PCT Pub. No.: WO2005/070315

PCT Pub. Date: Aug. 4, 2005

(65) Prior Publication Data

US 2007/0149964 A1 Jun. 28, 2007

(30) Foreign Application Priority Data

Jan. 27, 2004 (JP) .............................. 2004-018463

(51) Int. Cl.
*A61B 18/18* (2006.01)
*A61B 5/04* (2006.01)

(52) U.S. Cl. ........................................ 606/41; 600/374
(58) Field of Classification Search .................... 606/41, 606/58, 34, 45, 1, 32, 42, 48–50; 607/122, 607/14, 2, 115, 116, 119, 101–102; 600/393, 600/585, 381, 373, 374; 604/532, 523
See application file for complete search history.

(56) References Cited

U.S. PATENT DOCUMENTS

| | | | | |
|---|---|---|---|---|
| 5,275,162 A | * | 1/1994 | Edwards et al. | 600/374 |
| 5,313,943 A | * | 5/1994 | Houser et al. | 600/374 |
| 5,327,905 A | * | 7/1994 | Avitall | 600/585 |
| 5,354,297 A | * | 10/1994 | Avitall | 606/45 |

(Continued)

FOREIGN PATENT DOCUMENTS

CN          2082382 A          2/1994

(Continued)

OTHER PUBLICATIONS

Chinese Office Action (and English translation thereof) dated Mar. 21, 2008, issued in a counterpart Chinese Appliaction.

(Continued)

*Primary Examiner*—Michael Peffley
(74) *Attorney, Agent, or Firm*—Frishauf, Holtz, Goodman & Chick, P.C.

(57) ABSTRACT

A radiofrequency electric current ablation catheter comprising a tip electrode, a means for detecting temperature of the tip electrode, a catheter shaft and a portion for operation at proximal end, wherein the tip electrode has a shape formed by connecting three or more spherical or approximately spherical surfaces having centers on the same straight line to each other with a curved surface. The catheter has the tip electrode which has a small diameter, is brought into excellent contact with organisms, can provide a great output power and is easily cooled with the circulating blood stream.

16 Claims, 5 Drawing Sheets

U.S. PATENT DOCUMENTS

| | | | |
|---|---|---|---|
| 5,374,285 A * | 12/1994 | Vaiani et al. | 607/117 |
| 5,396,887 A * | 3/1995 | Imran | 600/374 |
| 5,400,783 A * | 3/1995 | Pomeranz et al. | 600/374 |
| 5,423,808 A * | 6/1995 | Edwards et al. | 606/34 |
| 5,423,882 A | 6/1995 | Jackman et al. | |
| 5,454,370 A * | 10/1995 | Avitall | 600/374 |
| 5,487,385 A | 1/1996 | Avitall | |
| 5,522,873 A * | 6/1996 | Jackman et al. | 607/122 |
| 5,642,736 A * | 7/1997 | Avitall | 600/585 |
| 5,688,266 A * | 11/1997 | Edwards et al. | 606/31 |
| 5,722,975 A * | 3/1998 | Edwards et al. | 606/34 |
| 5,743,903 A * | 4/1998 | Stern et al. | 606/31 |
| 5,779,669 A * | 7/1998 | Haissaguerre et al. | 604/95.01 |
| 5,897,552 A | 4/1999 | Edwards et al. | |
| 6,023,638 A * | 2/2000 | Swanson | 600/510 |
| 6,165,172 A * | 12/2000 | Farley et al. | 606/33 |
| 6,212,426 B1 * | 4/2001 | Swanson | 600/510 |
| 6,569,162 B2 * | 5/2003 | He | 606/41 |
| 2001/0041888 A1 * | 11/2001 | Goldman et al. | 606/32 |
| 2002/0007181 A1 * | 1/2002 | Zikorus et al. | 606/41 |
| 2003/0004506 A1 * | 1/2003 | Messing | 606/41 |
| 2003/0014037 A1 | 1/2003 | Thompson et al. | |

FOREIGN PATENT DOCUMENTS

| | | |
|---|---|---|
| JP | 8-503881 A | 4/1996 |
| JP | 9-506017 A | 6/1997 |
| JP | 8-503381 A | 4/1998 |
| WO | WO 01/74442 A1 | 10/2001 |

OTHER PUBLICATIONS

Japanese Office Action (and English translation thereof) dated Apr. 22, 2008, issued in a counterpart Japanese Application.

Supplementary European Search Report dated Jul. 11, 2008, issued in a counterpart European Application.

* cited by examiner

ABLATION CATHETER

This application is a U.S. National Phase Application under 35 USC 371 of International Application PCT/JP2005/001446 filed Jan. 26, 2005.

TECHNICAL FIELD

The present invention relates to an ablation catheter. More particularly, the present invention relates to an ablation catheter having a tip electrode which has a small diameter, is brought into excellent contact with organisms, can provide a great output power and is easily cooled with the circulating blood stream.

BACKGROUND ART

Arrhythmia takes place mainly due to formation of erethism at the heart and abnormal transfer of the formed erethism. From the standpoint of prognosis, the symptom of arrhythmia includes various cases ranging from cases which can be left without treatments to fatal cases. Arrhythmia causing degradation in the quality of life is treated for curing. Antiarrhythmic drugs such as Na channel blocking agent and K channel blocking agent were mainly used before. In 1982, the myocardial cautery using an ablation catheter was applied to the clinical treatment as a non-medicinal therapy. At present, development of a novel antiarrythmia drug is continued and, at the same time, improvement in the myocardial cautery is also continued.

In the percutaneous myocardial cautery, ablation catheters are inserted into the cardial cavity, and the tissue of the cardial muscle where the arrhythmia originates is destroyed or modified by applying heat between a tip electrode and an opposite electrode plate. This treatment is mainly applied to tachyarrhythmias such as paroxysmal supraventricular tachycardia, atrial tachycardia, atrial flutter and paroxysmal venticular tachycardia. As the first step, the cause of arrhythmia and the region of arrhythmia are investigated by the cardiac electrophysiological examination. The type and the circuit of arrhythmia are confirmed, and the optimal region for passing electric current is decided based on the result of the investigation. In the myocardial cautery, the tip electrode is pushed to the region causing the arrhythmia, and heating at 53 to 60° C. for about 60 seconds, for example, is repeated.

Figure 11:
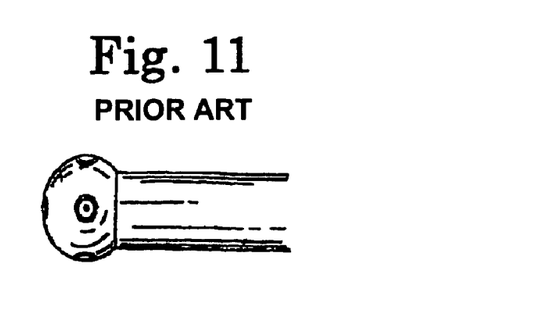
FIG. 11 shows a diagram exhibiting a side view of an example of conventional tip electrodes.
Figure 12:
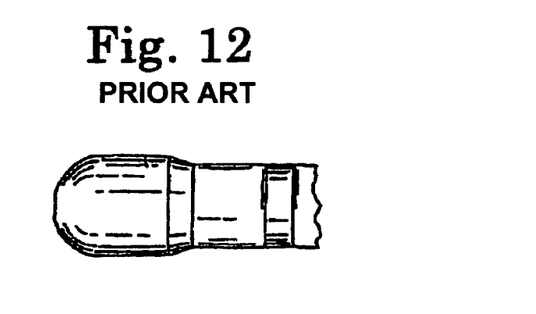
FIG. 12 shows a diagram exhibiting a side view of another example of conventional tip electrodes.
Figure 13:
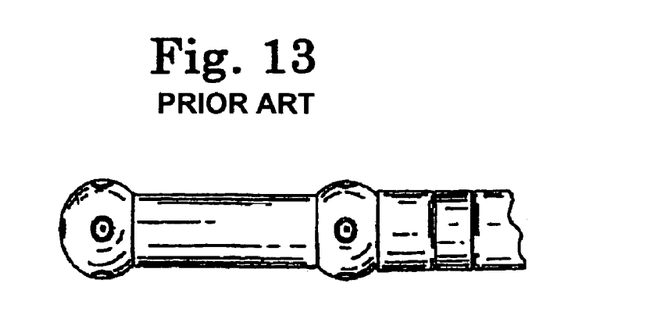
FIG. 13 shows a diagram exhibiting a side view of another example of conventional tip electrodes.
Figure 14:
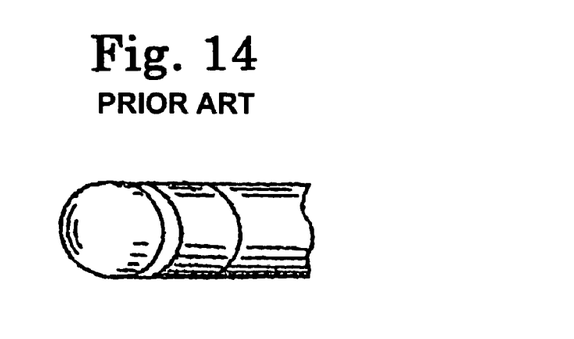
FIG. 14 shows a diagram exhibiting a perspective view of another example of conventional tip electrodes.

The spherical electrode having a single spherical shape shown in FIG. 11 and the cylindrical electrode having a spherical tip shown in FIG. 12, which are used widely at present, have small diameters and exhibit excellent operability. However, these electrodes have drawbacks in that the output power is small, the electrode cannot be brought into contact with or fixed to the organism sufficiently, the degree of cooling with the circulating blood stream is small, and cauterization is limited to the range of about 5 mm around the region pushed by the tip electrode. Therefore, these electrodes can be applied only to the treatment of monophyletic arrhythmias having a single cause the origin of which can be found in a narrow range and to the treatment of a conduction path passing through a very narrow portion. Application to deep regions in the ventricular wall is difficult although regions relatively close to the endocardium in the ventricular wall can be cauterized. Tip electrodes having two electrodes shown in FIGS. 13 and 14 are proposed. However, the effect of improvement in the contact with organisms and the cooling with the circulating blood stream is insufficient. Electrodes having a great dimension which are called large tip electrodes cause a decrease in the operability due to the great diameter of the electrode although the output power is great and the cooling with the circulating blood stream is improved. Therefore, an ablation catheter which has an electrode having a small diameter, exhibits excellent operability and can provide a great output power has been desired.

The present invention has an object of providing an ablation catheter having a tip electrode which has a small diameter, is brought into excellent contact with organisms, can provide a great output power and is easily cooled with the circulating blood stream.

DISCLOSURE OF THE INVENTION

As the result of extensive studies by the present inventors to achieve the above object, it was found that, when the tip electrode of the ablation catheter had a shape which was formed by connecting three or more spherical or approximately spherical surfaces having centers on the same straight line to each other with a curved surface, the surface area of the electrode could be increased to provide a great output power while the small diameter of the electrode was maintained, deep cauterization closed to that achieved by using a great spherical electrode could be achieved due to the exclusion effect of lines of electric force, and contact with and fixing to organisms could be improved due to the shape having three or more approximately spherical surfaces connected to each other. The present invention has been completed based on the knowledge.

The present invention provides:

(1) A radiofrequency electric current ablation catheter comprising a tip electrode, a means for detecting temperature of the tip electrode, a catheter shaft and a portion for operation at proximal end, wherein the tip electrode has a shape formed by connecting three or more spherical or approximately spherical surfaces having centers on a same straight line to each other with a curved surface;

(2) The ablation catheter described in (1), wherein at least one of the three or more spherical or approximately spherical surfaces is a surface selected from a spherical surface, a surface of an ellipsoid of revolution having an axis on a central axis of the catheter, an egg-shaped surface having an axis on a central axis of the catheter and a hemispherical surface having an axis on a central axis of the catheter;

(3) The ablation catheter described in any one of (1) and (2), wherein the tip electrode has a length of 0.5 to 15 mm and a maximum outer diameter of 0.5 to 3 mm;

(4) The ablation catheter described in (3), wherein, when an average diameter of adjacent two spherical or approximately spherical surfaces is represented by D and a distance between centers of the adjacent two spherical or approximately spherical surfaces is represented by d, d/D is 0.1 to 2 with respect to entire combinations of adjacent two spherical or approximately spherical surfaces;

(5) The ablation catheter described in (3), wherein, when an average diameter of adjacent two spherical or approximately spherical surfaces is represented by D and a distance between centers of the adjacent two spherical or approximately spherical surfaces is represented by d, d/D is 0.5 to 1.25 with respect to entire combinations of adjacent two spherical or approximately spherical surfaces;

(6) The ablation catheter described in any one of (1) and (2), wherein the tip electrode has a length of 1 to 12 mm and a maximum outer diameter of 1.0 to 2.7 mm;

(7) The ablation catheter described in (6), wherein, when an average diameter of adjacent two spherical or approximately spherical surfaces is represented by D and a distance between centers of the adjacent two spherical or approximately spherical surfaces is represented by d, d/D is 0.1 to 2 with respect to entire combinations of adjacent two spherical or approximately spherical surfaces; and (8) The ablation catheter described in (6), wherein, when an average diameter of adjacent two spherical or approximately spherical surfaces is represented by D and a distance between centers of the adjacent two spherical or approximately spherical surfaces is represented by d, d/D is 0.5 to 1.25 with respect to entire combinations of adjacent two spherical or approximately spherical surfaces.

In the figures, the mark 1 means a tip electrode, the mark 2 means a cavity, mark 3 means a tip electrode, the mark 4 means a catheter shaft, the mark 5 means a portion for operation at proximal end, the mark 6 means an electrode for measuring the electric potential, the mark 7 means a water tank kept at a constant temperature, the mark 8 means a heart of a pig, and the mark 9 means an apparatus for generating a radiofrequency electric current.

THE MOST PREFERRED EMBODIMENT TO CARRY OUT THE INVENTION

The ablation catheter of the present invention is a radiofrequency electric current ablation catheter comprising a tip electrode, a means for detecting temperature of the tip electrode, a catheter shaft and a portion for operation at proximal end, wherein the tip electrode has a shape formed by connecting three or more spherical or approximately spherical surfaces having centers on the same straight line to each other with a curved surface. In the present invention, the approximately spherical surface is not particularly limited as long as the surface has a shape which is wrapped with a surface having a shape close to a sphere. Examples of the shape include a surface of an ellipsoid of revolution having the axis on the central axis of the catheter; an egg-shaped surface having the axis on the central axis of the catheter; a surface which is formed from two truncated cones attached to each to other at the bottom portions and has the axis on the central axis of the catheter; a surface having a shape formed from a solid body, such as a cube and a polyhedron having a line connecting opposite apices or a line connecting intersections of diagonal lines of opposite two faces on the central axis of the catheter and a solid body having a curved surface, by rounding so that the solid body can be wrapped with a spherical surface, a surface of an ellipsoid of revolution or an egg-shaped surface having the axis on the central axis of the catheter or by forming into a curved surface having the axis on the central axis of the catheter; a hemispherical surface formed by approximately bisecting a spherical surface by a plane perpendicular to the central axis of the catheter; and a surface formed by approximately bisecting a surface of an ellipsoid of revolution or an egg-shaped surface by a plane perpendicular to the central axis of the catheter.

In the present invention, when the average diameter of adjacent two spherical or approximately spherical surfaces is represented by D and the distance between the centers of adjacent two spherical or approximately spherical surfaces is represented by d, it is preferable that d/D is 0.1 to 2 and more preferably 0.5 to 1.25 with respect to the entire combinations of adjacent two spherical or approximately spherical surfaces. The average diameter means the arithmetic average obtained from the diameters of adjacent two spherical or approximately spherical surfaces, wherein the diameter is the diameter of a spherical surface or the "diameter" of an approximately spherical surface. In the present invention, the "diameter" of an approximately spherical surface used for calculation of the average diameter D is defined as follows. When the surface is a surface of an ellipsoid of revolution having the axis on the central axis of the catheter or an egg-shaped surface having the axis on the central axis of the catheter, the average diameter is calculated by using the "diameter" placed on the central axis. When the surface is a surface which is formed from two truncated cones attached to each to other at the bottom portions and has the axis on the central axis of the catheter; or a surface having a shape formed from a solid body, such as a cube and a polyhedron having a line connecting opposite apices or a line connecting intersections of diagonal lines of opposite two faces on the central axis of the catheter and a solid body having a curved surface, by rounding so that the solid body can be wrapped with a spherical surface, a surface of an ellipsoid of revolution or an egg-shaped surface having the axis on the central axis of the catheter or by forming into a curved surface having the axis on the central axis of the catheter, the average diameter is calculated by using the diameter of the spherical surface or the "diameter" of the surface of an ellipsoid of revolution or the egg shaped surface placed on the central axis. When the surface is a hemispherical surface formed by approximately bisecting a spherical surface by a plane perpendicular to the central axis of the catheter, the average diameter is calculated by using the diameter of the spherical surface. When the surface is a hemispherical surface formed by approximately bisecting a surface of an ellipsoid of revolution or an egg-shaped surface having the axis on the central axis of the catheter by a plane perpendicular to the central axis of the catheter, the average diameter is calculated by using the "diameter" of the surface of an ellipsoid of revolution or the egg-shaped surface placed on the central axis. In the present invention, it is preferable that the ratio of the "diameter" of the surface of an ellipsoid of revolution or the egg-shaped surface placed on the central axis of the catheter as defined above to the maximum diameter of the circle of the section obtained by cutting the surface by a plane perpendicular to the central axis of the catheter is 0.7 to 1.3 and more preferably 0.85 to 1.15. The position of the center of the approximately spherical surface used for calculation of the distance between the centers of the adjacent two spherical or approximately spherical surfaces is defined as the position of the center of the circle of the section providing the maximum diameter among circles of the section obtained by cutting the surface by a plane perpendicular to the central axis of the surface of an ellipsoid of revolution or the egg-shaped surface.

Figure 1:
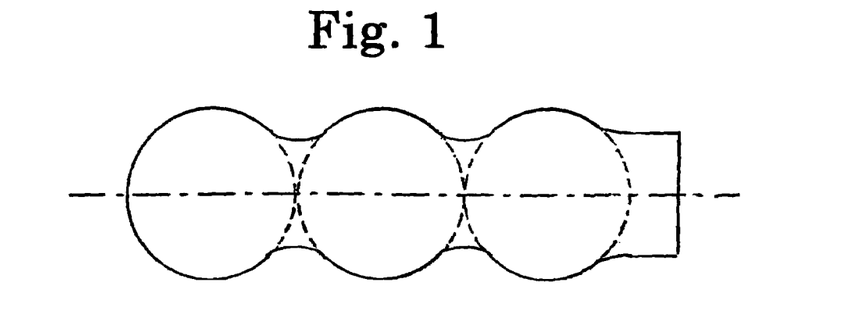
FIG. 1 shows a diagram exhibiting an embodiment of the shape of the tip electrode of the ablation catheter of the present invention.
Figure 2:
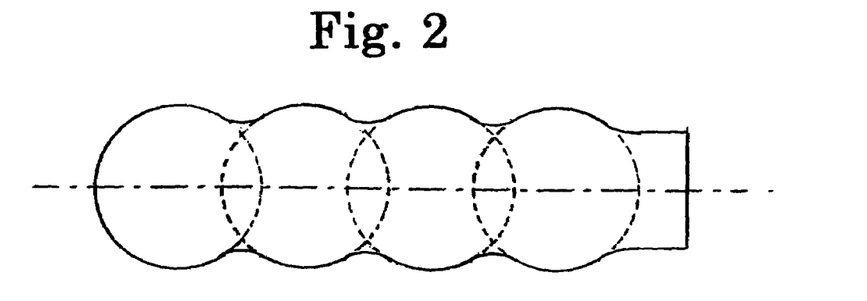
FIG. 2 shows a diagram exhibiting another embodiment of the shape of the tip electrode.
Figure 3:
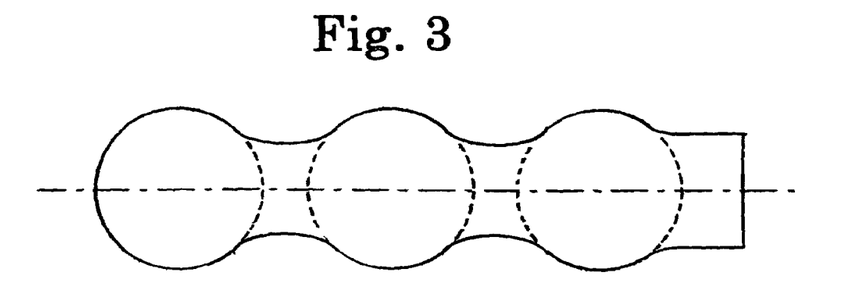
FIG. 3 shows a diagram exhibiting another embodiment of the shape of the tip electrode.

FIG. 1 shows a diagram exhibiting an embodiment of the shape of the tip electrode of the ablation catheter of the present invention. In the present embodiment, three spherical surfaces having the centers on the central axis of the tip electrode are connected to each other with a smooth curved surface. In FIG. 1 and FIGS. 2 to 7 which follow, an approximately spherical surface is shown by a partially solid and partially broken line, and the surface of the tip electrode is shown by an entirely solid line. In the present embodiment, the value of d/D is 1.0. FIG. 2 shows a diagram exhibiting another embodiment of the shape of the tip electrode of the ablation catheter. In the present embodiment, four spherical surfaces having the centers on the central axis of the tip electrode are connected to each other with a smooth curved surface. In the present embodiment, the value of d/D is 0.75. FIG. 3 shows a diagram exhibiting another embodiment of the shape of the tip electrode of the ablation catheter. In the present embodiment, three spherical surfaces having the centers on the central axis of the tip electrode are connected to each other with a smooth curved surface. In the present embodiment, the value of d/D is 1.25.

Figure 4:
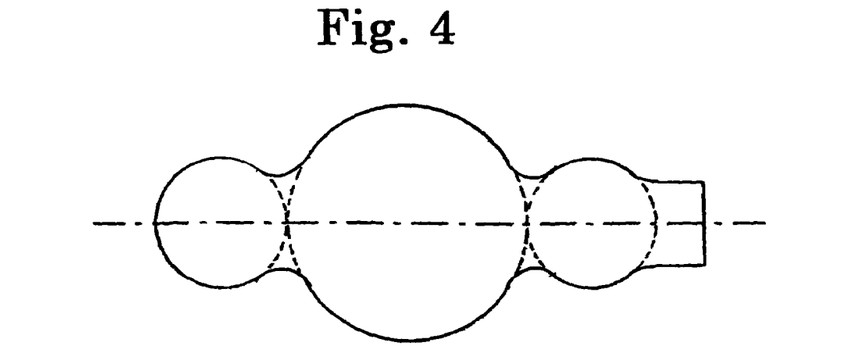
FIG. 4 shows a diagram exhibiting another embodiment of the shape of the tip electrode.

In the present invention, it is not necessary that three or more approximately spherical surfaces forming the tip electrode have the same size. The tip electrode may have a shape formed by connecting three or more approximately spherical surfaces having different sizes to each other. FIG. 4 shows a diagram exhibiting another embodiment of the shape of the tip electrode of the ablation catheter. In the present embodiment, two smaller spherical surfaces and one greater spherical surface having the centers on the central axis of the tip electrode are connected to each other with a smooth curved surface. In the embodiment, the value of d/D is 1.11.

Figure 5:
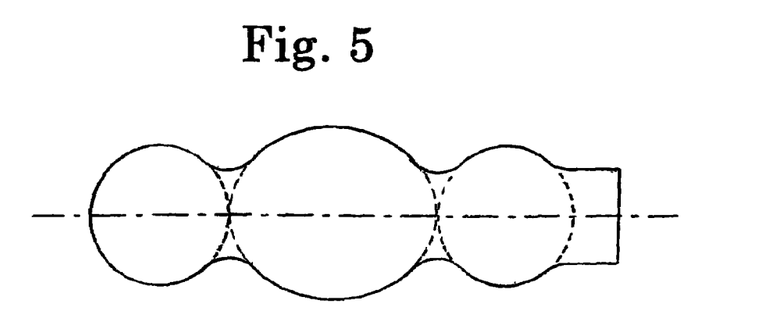
FIG. 5 shows a diagram exhibiting another embodiment of the shape of the tip electrode.
Figure 6:
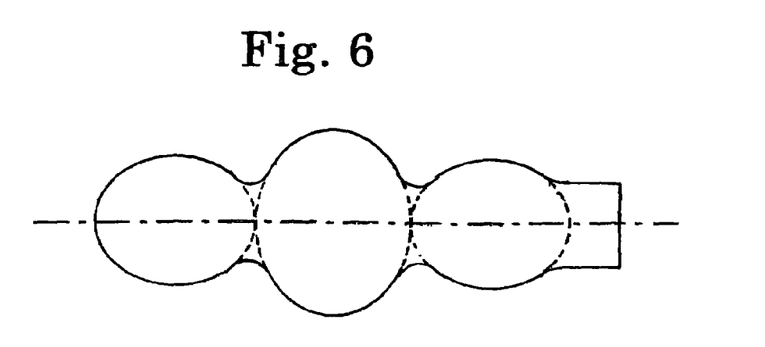
FIG. 6 shows a diagram exhibiting another embodiment of the shape of the tip electrode.

FIG. 5 shows a diagram exhibiting another embodiment of the shape of the tip electrode of the ablation catheter. In the present embodiment, two spherical surfaces and one surface of an ellipsoid of revolution having the centers on the central axis of the tip electrode are connected to each other with a smooth curved surface. As defined above, the average diameter of the approximately spherical surface is calculated by using the diameter placed on the central axis as the diameter of the surface of an ellipsoid of revolution. In the present invention, the value of d/D is 1.07. FIG. 6 shows a diagram exhibiting another embodiment of the shape of the tip electrode of the ablation catheter of the present invention. In the present embodiment, two surfaces of an ellipsoid of revolution having the major axis on the central axis of the tip electrode 1 and one surface of an ellipsoid of revolution having the minor axis on the central axis of the tip electrode are connected to each other with a smooth surface. In the present invention, the value of d/D is 0.96.

Figure 7:
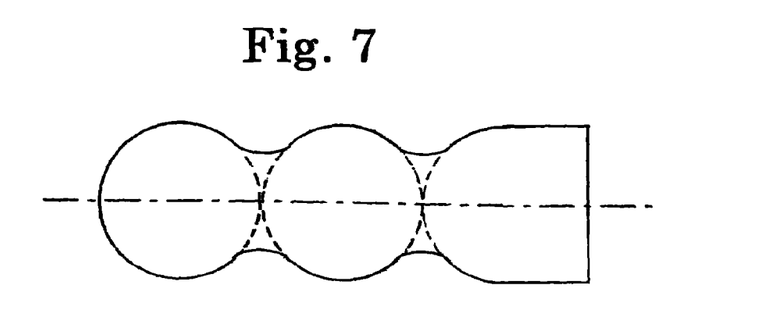
FIG. 7 shows a diagram exhibiting another embodiment of the shape of the tip electrode.

In the present invention, it is not necessary that the three or more approximately spherical surfaces forming the tip electrode have all complete approximately spherical surfaces. For example, a hemispherical surface may be used. FIG. 7 shows a diagram exhibiting another embodiment of the shape of the tip electrode. In the present embodiment, the third approximately spherical surface from the tip has a hemispherical shape. Since the hemispherical surface is regarded as the approximately spherical surface, the tip electrode of the embodiment shown in FIG. 7 has the shape formed by connecting three or more approximately spherical surfaces having the centers on the same straight line to each other with a curved surface. In the present invention, the value of d/D is 1.0.

Figure 8:
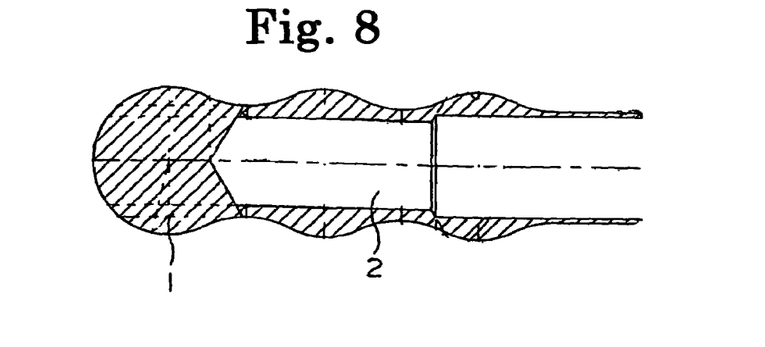
FIG. 8 shows a diagram exhibiting a sectional view of another embodiment of the tip electrode of the ablation catheter of the present invention.

FIG. 8 shows a diagram exhibiting a sectional view of another embodiment of the tip electrode of the ablation catheter of the present invention. The tip electrode of the present embodiment has approximately the same shape as that of the tip electrode of the embodiment shown in FIG. 1, and the value of d/D is 1.0. In the present embodiment, a cavity 2 is formed at the inside of the tip electrode 1. A means for detecting the temperature and a lead wire for the electrode which is used for introducing radio frequency electric current to the tip electrode are disposed in this cavity.

Since the tip electrode of the ablation catheter of the present invention has a smoothly undulated shape formed by connecting three or more approximately spherical surfaces to each other with a curved surface, the tip electrode is excellently brought into contact with and fixed to organisms and easily placed into folded portions of the wall of the cardial cavity. Therefore, the tip electrode can be pushed with stability to achieve the myocardial cautery. Since the tip electrode has the smooth shape formed by connecting three or more approximately spherical surfaces to each other with a curved surface and is cooled with the circulating blood stream, coagulation of blood causing thrombosis can be suppressed. Since the tip electrode of the ablation catheter of the present invention has a greater surface area than that of a cylindrical electrode having a spherical tip and provides an output power as great as that obtained by using a large tip electrode, a region having a great area can be cauterized to a great depth. In the tip electrode having the shape formed by connecting three or more approximately spherical surfaces to each other with a curved surface, the strongest line of electric force is emitted from the outermost circumferential portion of each approximately spherical surface. In other words, virtually three lines of electric force are emitted from the tip electrode having the shape formed by connecting three approximately spherical surfaces to each other with a curved surface. Since the lines of electric force repel each other due to the exclusion effect of lines of electric force, the output power at the center is enhanced. The line of electric force at the center penetrates a tissue of an organism directly into deep regions, and the cauterization is achieved effectively.

In the present invention, as described above, the approximately spherical shape constituting the tip electrode can be further modified from the complete shape of the spherical surface, the surface of an ellipsoid of revolution or the egg-shaped surface. Examples of the modified shape include a shape formed from two truncated cones attached to each there at the bottom portions and rounded and a shape of a cube rounded to a great degree. When a shape is formed by connecting three or more relatively uniform blocks each covered with a curved surface to each other at suitable distances from each other, the surface area of the electrode can be increased without increasing the outer diameter of the electrode, and the effect close to that of a large tip electrode can be exhibited due to the exclusion effect of the lines of electric force between the blocks while the electric potential at the central portion is not decreased so much as that of a cylindrical tip electrode having a spherical tip which is obtained by just increasing the length of an electrode having a single spherical surface. However, when the shape is greatly deformed from the spherical shape and sharp points are formed, there is the possibility that electric charges are concentrated at the sharp points to cause an abnormal increase in the temperature, and side effects such as thrombosis and damages of tissues take place.

In the present invention, it is preferable that the length of the tip electrode is 0.5 to 15 mm and more preferably 1 to 12 mm. When the length of the tip electrode is shorter than 0.5 mm, there is the possibility that the output power necessary for the myocardial cautery using the catheter is not obtained. When the length exceeds 15 mm, there is the possibility that operability of the ablation catheter deteriorates.

Examples of the material of the tip electrode used in the present invention include gold, stainless steel, platinum, platinum-iridium alloys, platinum-tungsten alloys and nickel-titanium shape memory alloys. Among these materials, platinum is preferable since platinum has been used frequently for organisms, and the safety has been confirmed. The means for detecting the temperature used in the present invention is not particularly limited. Examples include alumel/chromel thermocouples and thermisters.

Figure 9:
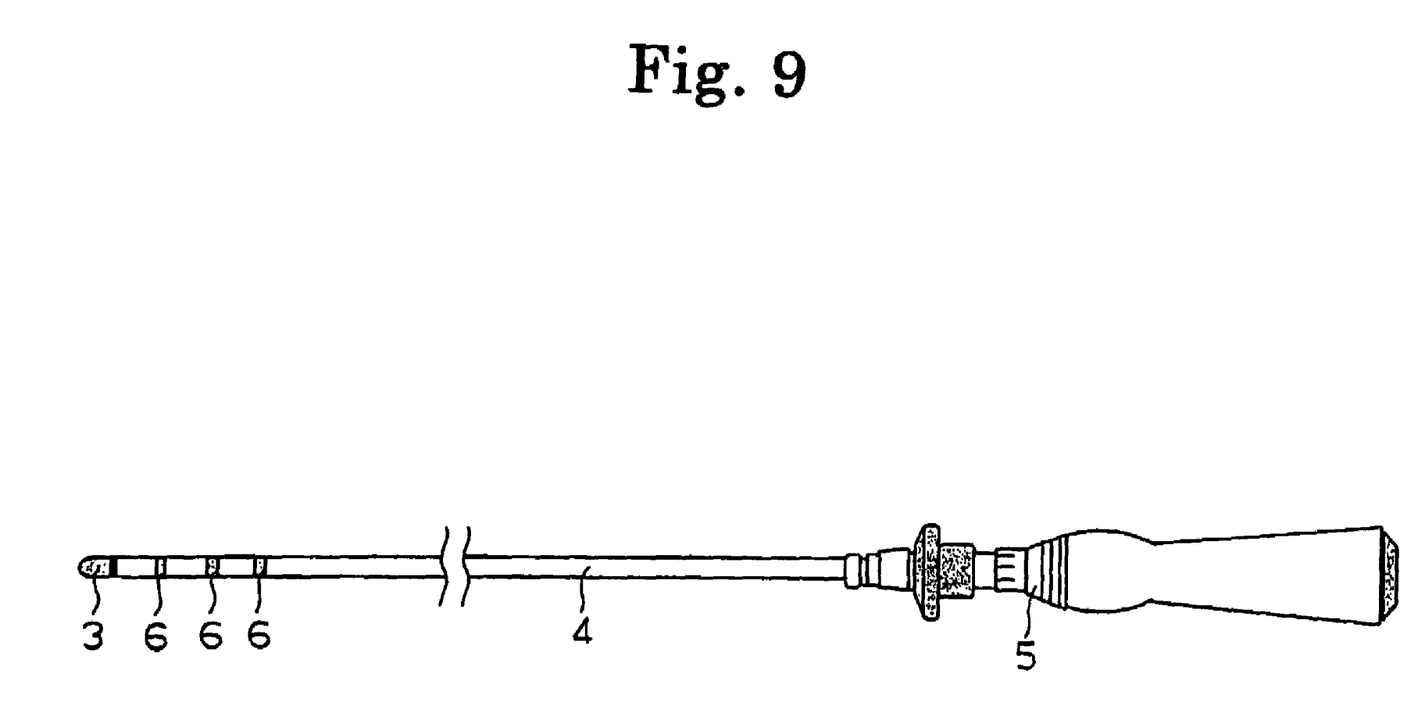
FIG. 9 shows a diagram exhibiting a side view of an embodiment of the ablation catheter of the present invention.

FIG. 9 shows a diagram exhibiting a side view of an embodiment of the ablation catheter of the present invention. The ablation catheter of the present embodiment has a tip electrode 3, a catheter shaft 4 and a portion for operation at proximal end 5, and a means for detecting temperature of the tip electrode is disposed in a cavity of the tip electrode. As for the material of the catheter shaft, for example, a construction having an outermost layer comprising a polyurethane or a polyamide having a D hardness of 40 to 70, an intermediate layer comprising a net or a coil of a metal as the reinforcement and an innermost layer comprising a polyimide having excellent mechanical and electric properties can be used. The above construction can be formed by knitting or winding metal wires on the surface of a plastic tube forming the inner most layer, followed by applying a coating material to the surface. It is preferable that the distal end portion of the catheter shaft is formed with an elastomer so that the distal end portion can be freely bent as desired. In the cavity at the inside of the innermost layer, a plurality of lumens are disposed, and a lead wire for the electrode used for supplying the radio frequency electric current to the tip electrode, a lead wire for connecting the means for detecting the temperature of the tip electrode to the portion for operation at proximal end and tension wires used for the bending operation of the distal end portion of the catheter shaft can be inserted through the lumens. As a lumen at the inside of the cavity of the innermost layer, a lumen for passing cooling water may be disposed.

In the ablation catheter of the present invention, it is preferable that the maximum value of the outer diameter of the tip electrode is 0.5 to 3 mm and more preferably 1.0 to 2.7 mm. When the maximum value of the outer diameter of the tip electrode is smaller than 0.5 mm, there is the possibility that securing the space necessary for disposing the lead wires for the electrode and thermocouples becomes difficult. When the maximum value of the outer diameter of the tip electrode exceeds 3 mm, there is the possibility that insertion into femoral vein becomes difficult.

In the ablation catheter of the present invention, it is preferable that an electrode 6 for measuring the electric potential is disposed at the distal end of the catheter shaft. The ablation catheter is inserted into the cardial cavity under watching using X-ray. Pacing stimuli are sent from the ventricle and the atrium by the operation at the portion for operation at proximal end to induce paroxysmal tachycardia, and mapping of the portion of the valve ring where the auxiliary conducting path is attached is conducted. Using the electric potential in the cardial cavity measured by an electrode for measuring the electric potential disposed at the distal end portion of the catheter as the indicator, the optimum portion for ablation is decided, and a radio frequency electric current is passed. The degree of penetration into a tissue of an organism is greater when the frequency of the radio frequency electric current is lower. However, a radio frequency electric current in the region of 500 kHz is used since the cell membrane is excited due to the Faraday effect to cause arrhythmia when the frequency is lower than 300 kHz. It is preferable that the output power is 20 to 50 W, and the temperature of the tip electrode is 50 to 60° C. When the radio frequency electric current is passed through the optimum region, the conduction at the auxiliary conduction path breaks off within several seconds. When the passage of the electric current is completed, it is confirmed by the clinical cardiac electrophysiological test that there is no possibility of relapse. Thus, the operation can be completed.

EXAMPLES

The present invention will be described more specifically with reference to examples in the following. However, the present invention is not limited to the examples.

Example 1

An ablation catheter equipped with a tip electrode having a shape shown in FIG. 8 and a construction shown in FIG. 9 was prepared. The tip electrode had a length of 8.0 mm, was made of platinum and had a shape such that three spherical surfaces having a diameter of 2.6 mm were arranged on the same straight line at a distance between the centers of 2.6 mm and the three spherical surfaces and the portion of the catheter shaft adjacent to the third spherical surface were connected to each other with a smooth surface. The catheter shaft had an effective length of 1,100 mm and an outer diameter of 2.4 mm, and the materials for the catheter shaft were a polyamide resin reinforced with braids of stainless steel for the portion at proximal end and a polyamide polyether elastomer for the bending portion at distal end. As the means for detecting the temperature of the tip electrode, an alumel/chromel thermocouple was disposed at the inside of the tip electrode. Three electrodes made of platinum for measuring the electric potential were attached to the catheter shaft at a distance of 2 mm between each other from the tip electrode towards the portion at proximal end. A pair of wires running at the inside of the cavity of the tube from the portion for operation at proximal end to the distal end portion of the catheter shaft were disposed so that the distal end portion could be bent by pulling the wires by the operation of a handle at the portion for operation at proximal end. The tip electrode and the apparatus for generating radio frequency electric current were connected to each other through a lead wire for the electrode.

Figure 10:
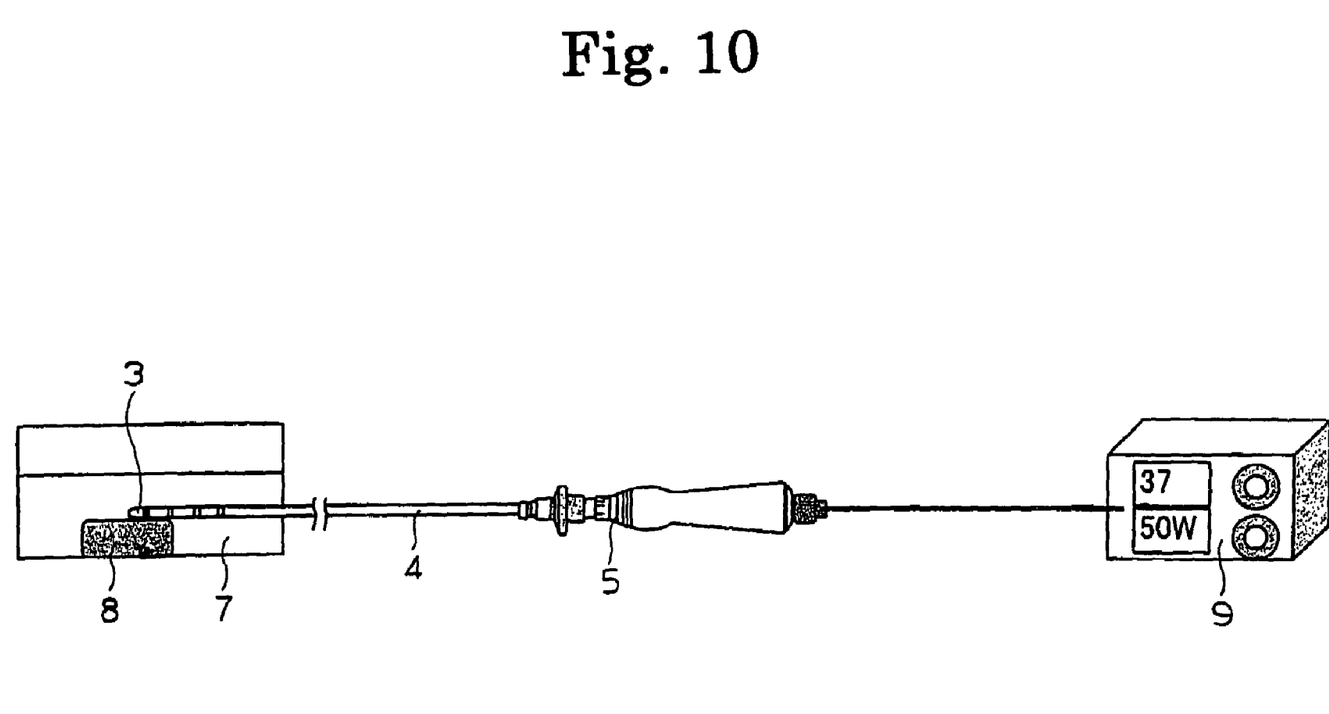
FIG. 10 shows a diagram exhibiting the apparatus used for the cauterization test.

FIG. 10 shows a diagram exhibiting the apparatus used for the cauterization test. An opposite electrode plate was placed at the bottom of a water tank 7 kept at a constant temperature of 37° C. and filled with physiological saline. A heart of a pig 8 was placed on the opposite electrode plate, and the tip electrode 3 of the ablation catheter was pushed to the heart of a pig. A radio frequency electric current of 500 kHz was passed from the apparatus for generating radio frequency electric current 9. When the output power was increased to 50 W, the temperature at the inside of the tip electrode measured by the thermocouple reached 60° C. After the cauterization was conducted under this condition for 60 seconds, the electric current was stopped for 5 minutes. This operation was conducted four times.

After the cauterization test was completed, the heart of a pig was taken out, and the cauterized region was examined. The cauterized region had a surface area of 120 mm² and a depth of 7 mm.

Comparative Example 1

The cauterization test of a heart of a pig was conducted in accordance with the same procedures as those conducted in Example 1 except that a cylindrical electrode having a spherical tip which had a shape shown in FIG. 12, a diameter of the spherical surface at the tip of 2.6 mm and a length of 3.5 mm was used as the tip electrode.

When the output power of the radio frequency electric current of 500 kHz was increased to 35 W, the temperature at the inside of the tip electrode measured by the thermocouple reached 60° C. The cauterization was conducted 5 times each for 60 seconds under this condition similarly to that conducted in Example 1.

After the cauterization test was completed, the heart of a pig was taken out, and the cauterized region was examined. The cauterized region had a surface area of 75 mm² and a depth of 5 mm.

Comparative Example 2

The cauterization test of a heart of a pig was conducted in accordance with the same procedures as those conducted in Example 1 except that a large tip electrode having a diameter of the spherical surface of 5.0 mm was used as the tip electrode.

When the output power of the radio frequency electric current of 500 kHz was increased to 45 W, the temperature at the inside of the tip electrode measured by the thermocouple reached 60° C. The cauterization was conducted 5 times each for 60 seconds under this condition similarly to that conducted in Example 1.

After the cauterization test was completed, the heart of a pig was taken out, and the cauterized region was examined. The cauterized region had a surface area of 100 mm² and a depth of 6 mm.

The results in Example 1 and Comparative Examples 1 and 2 are shown in Table 1.

TABLE 1

| | Tip electrode | Output power (W) | Cauterized region surface area (mm²) | depth (mm) |
|---|---|---|---|---|
| Example 1 | 3 spherical surfaces having a diameter of 2.6 mm | 50 | 120 | 7 |
| Comparative Example 1 | cylinder having a spherical surface having a diameter of 2.6 mm at the tip | 35 | 75 | 5 |
| Comparative Example 2 | large tip having a diameter of 5.0 mm | 45 | 100 | 6 |

As shown in Table 1, the ablation catheter used in Example 1 which was equipped with the tip electrode having a shape formed by connecting three spherical surfaces to each other with a curved surface could achieve the cauterization at a greater output power. The cauterization was achieved over a greater area into a deeper region. Thus, it was shown that the ablation catheter of the present invention exhibited the property for cauterization more excellent than that of the ablation catheter equipped with the large tip electrode exhibiting insufficient operability while the excellent operability was maintained.

INDUSTRIAL APPLICABILITY

Since the ablation catheter of the present invention has a tip electrode having a shape formed by connecting three spherical surfaces having the centers on the same straight line to each other with a curved surface, operability is excellent due to the small diameter of the electrode, stable use can be achieved due to the excellent contact with organisms, a great output power can be obtained, the energy reaches to deep regions due to the exclusion effect of lines of electric force, cooling with the circulating blood stream is easily achieved, and thrombosis is suppressed. Cases to which the percutaneous catheter myocardial cautery can be applied are increased and excellent results can be obtained by using the ablation catheter of the present invention.

The invention claimed is:

1. A radio-frequency electric current ablation catheter comprising:
   a tip electrode;
   a unit which detects a temperature of the tip electrode;
   a catheter shaft; and
   an operating portion at a proximal end,
   wherein the tip electrode is formed of a single metallic body and a surface of the tip electrode comprises at least three spherical or approximately spherical surfaces which have centers on a same straight line and a reduced-diameter portion provided between each of the adjacent spherical or approximately spherical surfaces such that the adjacent spherical or approximately spherical surfaces are connected by a curved surface and are unbroken without any gaps or apertures formed anywhere on the surface of the tip electrode, wherein each said reduced-diameter portion has an outer diameter that is less than an outer diameter of each of the spherical or approximately spherical surfaces.

2. The ablation catheter according to claim 1, wherein at least one of the spherical or approximately spherical surfaces is a surface selected from a spherical surface, a surface of an ellipsoid of revolution having an axis on a central axis of the catheter, an egg-shaped surface having an axis on the central axis of the catheter and a hemispherical surface having an axis on the central axis of the catheter.

3. The ablation catheter according to claim 2, wherein the tip electrode has a length of 1 to 12 mm and a maximum outer diameter of 1 to 2.7 mm.

4. The ablation catheter according to claim 3, wherein an average diameter of two adjacent spherical or approximately spherical surfaces is represented by D, a distance between the centers of the two adjacent spherical or approximately spherical surfaces is represented by d, and d/D is 0.1 to 2 for each combination of two adjacent spherical or approximately spherical surfaces.

5. The ablation catheter according to claim 3, wherein an average diameter of two adjacent spherical or approximately spherical surfaces is represented by D, a distance between the centers of the two adjacent spherical or approximately spherical surfaces is represented by d, and d/D is 0.5 to 1.25 for each combination of two adjacent spherical or approximately spherical surfaces.

6. The ablation catheter according to claim 2, wherein the tip electrode has a length of 0.5 to 15 mm and a maximum outer diameter of 0.5 to 3 mm.

7. The ablation catheter according to claim 6, wherein an average diameter of two adjacent spherical or approximately spherical surfaces is represented by D, a distance between the centers of the two adjacent spherical or approximately spherical surfaces is represented by d, and d/D is 0.1 to 2 for each combination of two adjacent spherical or approximately spherical surfaces.

8. The ablation catheter according to claim 6, wherein an average diameter of two adjacent spherical or approximately spherical surfaces is represented by D, a distance between the centers of the two adjacent spherical or approximately spherical surfaces is represented by d, and d/D is 0.5 to 1.25 for each combination of two adjacent spherical or approximately spherical surfaces.

9. The ablation catheter according to claim 1, wherein the tip electrode has a length of 0.5 to 15 mm and a maximum outer diameter of 0.5 to 3 mm.

10. The ablation catheter according to claim 9, wherein an average diameter of two adjacent spherical or approximately spherical surfaces is represented by D, a distance between the centers of the two adjacent spherical or approximately spherical surfaces is represented by d, and d/D is 0.1 to 2 for each combination of two adjacent spherical or approximately spherical surfaces.

11. The ablation catheter according to claim 9, wherein an average diameter of two adjacent spherical or approximately spherical surfaces is represented by D, a distance between the centers of the two adjacent spherical or approximately spherical surfaces is represented by d, and d/D is 0.5 to 1.25 for each combination of two adjacent spherical or approximately spherical surfaces.

12. The ablation catheter according to claim 1, wherein the tip electrode has a length of 1 to 12 mm and a maximum outer diameter of 1 to 2.7 mm.

13. The ablation catheter according to claim 12, wherein an average diameter of two adjacent spherical or approximately spherical surfaces is represented by D, a distance between the centers of the two adjacent spherical or approximately spherical surfaces is represented by d, and d/D is 0.1 to 2 for each combination of two adjacent spherical or approximately spherical surfaces.

14. The ablation catheter according to claim 12, wherein an average diameter of two adjacent spherical or approximately spherical surfaces is represented by D, a distance between the centers of the two adjacent spherical or approximately spherical surfaces is represented by d, and d/D is 0.5 to 1.25 for each combination of two adjacent spherical or approximately spherical surfaces.

15. The ablation catheter according to claim 1, wherein a shape of a longitudinal section of the curved surface is a smoothly curved line, a first end of the curved line is tangent to a circle or an approximate circle which is a shape of a longitudinal section of one of the adjacent spherical or approximately spherical surfaces, a second end of said curved line is tangent to another circle or approximate circle which is a shape of a longitudinal section of another of the adjacent spherical or approximately spherical surfaces, and the curved line is closest to said straight line at an approximately middle point between the first and second ends.

16. The ablation catheter according to claim 1, wherein the tip electrode is formed of a material selected from the group consisting of gold, stainless steel, platinum, platinum-iridium alloys, platinum-tungsten alloys, and nickel-titanium shape memory alloys.

* * * * *